(12) United States Patent
Naniki et al.

(10) Patent No.: US 9,586,927 B2
(45) Date of Patent: Mar. 7, 2017

(54) METHOD FOR CONTINUOUSLY PRODUCING CYCLIC CARBONATE

(71) Applicants: MARUZEN PETROCHEMICAL CO., LTD., Chuo-ku (JP); NATIONAL INSTITUTE OF ADVANCED INDUSTRIAL SCIENCE AND TECHNOLOGY, Chiyoda-ku (JP)

(72) Inventors: Takashi Naniki, Ichihara (JP); Yasunori Hayashi, Ichihara (JP); Goro Sawada, Ichihara (JP); Takuro Furukawa, Ichihara (JP); Takeshi Haruna, Ichihara (JP); Toshikazu Takahashi, Tsukuba (JP); Hiroyuki Yasuda, Tsukuba (JP); Shouji Yamamoto, Tsukuba (JP)

(73) Assignees: MARUZEN PETROCHEMICAL CO., LTD., Chuo-ku (JP); National Institute of Advanced Industrial Science and Technology, Chiyoda-ku (JP)

( * ) Notice: Subject to any disclaimer, the term of this patent is extended or adjusted under 35 U.S.C. 154(b) by 0 days.

(21) Appl. No.: 14/903,225

(22) PCT Filed: Jul. 18, 2014

(86) PCT No.: PCT/JP2014/069151
§ 371 (c)(1),
(2) Date: Jan. 6, 2016

(87) PCT Pub. No.: WO2015/008853
PCT Pub. Date: Jan. 22, 2015

(65) Prior Publication Data
US 2016/0168112 A1 Jun. 16, 2016

(30) Foreign Application Priority Data

Jul. 19, 2013 (JP) ................. 2013-150334

(51) Int. Cl.
*C07D 317/08* (2006.01)
*C07D 317/38* (2006.01)
*B01J 31/02* (2006.01)

(52) U.S. Cl.
CPC ........ *C07D 317/38* (2013.01); *B01J 31/0231* (2013.01); *B01J 31/0239* (2013.01); *B01J 31/0254* (2013.01); *B01J 31/0268* (2013.01); *B01J 31/0269* (2013.01); *B01J 31/0271* (2013.01); *B01J 2231/341* (2013.01)

(58) Field of Classification Search
CPC .................................................... C07D 317/38
USPC ........................................................ 549/230
See application file for complete search history.

(56) References Cited

U.S. PATENT DOCUMENTS

| 4,314,945 A | 2/1982 | McMullen et al. |
| 2007/0213542 A1 | 9/2007 | Van Der Heide et al. |
| 2008/0214386 A1 | 9/2008 | Takahashi et al. |
| 2009/0221840 A1 | 9/2009 | Yamagishi et al. |

FOREIGN PATENT DOCUMENTS

| CN | 1926125 A | 3/2007 |
| CN | 101553479 A | 10/2009 |
| CN | 102060657 A | 5/2011 |
| JP | 55-145623 A | 11/1980 |
| JP | 63-017072 B2 | 4/1988 |
| JP | 03-120270 A | 5/1991 |
| JP | 9-227550 A | 9/1997 |
| JP | 2002-363177 A | 12/2002 |
| JP | 2004-250349 A | 9/2004 |
| JP | 2007-284427 A | 11/2007 |
| JP | 2008-296066 A | 12/2008 |
| WO | WO 2005/084801 A1 | 9/2005 |
| WO | WO 2005/085224 A1 | 9/2005 |

OTHER PUBLICATIONS

International Search Report issued Oct. 7, 2014, in PCT/JP2014/069151 filed Jul. 18, 2014.
Combined Chinese Office Action and Search Report issued Aug. 18, 2016 in Patent Application No. 201480039970.0 (with English Translation of Categories of Cited Documents).

*Primary Examiner* — Nizal Chandrakumar
(74) *Attorney, Agent, or Firm* — Oblon, McClelland, Maier & Neustadt, L.L.P.

(57) ABSTRACT

Provided is a method for continuously producing a cyclic carbonate, by which generation of a glycol in a reaction for synthesizing a cyclic carbonate is suppressed, and a cyclic carbonate having a high purity can be efficiently obtained even by simple purification.
A method for continuously producing a cyclic carbonate, including filling a catalyst in a fixed-bed tube reactor, and continuously feeding carbon dioxide and an epoxide to the fixed-bed tube reactor to thereby bringing the carbon dioxide and the epoxide into contact with the catalyst, while continuously withdrawing the reaction liquid in the fixed-bed tube reactor, wherein the method includes a pre-treatment step in which a pre-treatment liquid containing a cyclic carbonate is brought into contact with the catalyst before feeding the carbon dioxide and the epoxide to the fixed-bed tube reactor, and the generated glycol is removed out of the system.

5 Claims, 3 Drawing Sheets

* Reaction time denotes the time after the start of ethylene oxide supply.

* Reaction time denotes the time after the start of ethylene oxide supply.

METHOD FOR CONTINUOUSLY PRODUCING CYCLIC CARBONATE

TECHNICAL FIELD

The present invention relates to a method for continuously producing a cyclic carbonate.

BACKGROUND ART

Cyclic carbonates are used as organic solvents, agents for processing synthetic fibers, raw materials for medicaments, cosmetic additives and electrolyte solvents for lithium batteries, and are also utilized for the synthesis of alkylene glycols and dialkyl carbonates, and the like (Patent Literature 1), and thus are one of important compounds that are used in a wide variety of applications.

Conventionally, the cyclic carbonates have been synthesized by reacting an epoxide and carbon dioxide in the presence of a homogeneous system catalyst under a suitable pressurized condition. As such homogeneous system catalyst, halides of alkali metals and onium salts such as quaternary ammonium salts have been conventionally known (Patent Literature 2), and are industrially used.

However, in the case when such homogeneous system catalyst is used, a separation operation to separate the reaction mixture and catalyst by distillation, or the like is generally required, and thus the production steps become complex, and there are problems of the decomposition of the catalyst during the separation step and the generation of by-products.

Therefore, for the purpose of simplifying the catalyst separation process, a heterogenous catalyst in which quaternary phosphonium each having a halide ion as a counterion are immobilized on a support such as a silica gel, and a heterogenous catalyst in which an alkali metal element or an alkaline earth metal element has been formed into a composite oxide with phosphorus, silica or the like, have been suggested (Patent Literatures 3 to 5).

CITATION LIST

Patent Literature

Patent Literature 1: JP S55-145623 A
Patent Literature 2: JP S63-17072 B
Patent Literature 3: WO 2005/084801 A
Patent Literature 4: JP 2008-296066 A
Patent Literature 5: WO 2005/085224 A
Patent Literature 6: JP H9-227550 A
Patent Literature 7: JP 2007-284427 A

SUMMARY OF INVENTION

Solution to Problem

However, water in the air is adsorbed by these heterogenous catalysts during production and storage. In the case when a reaction of an epoxide and carbon dioxide is performed while water is adsorbed by a catalyst, a glycol is generated by the side reaction of the epoxide and water, and thus there is a problem that it is difficult to obtain a cyclic carbonate having a high purity, or it is necessary to separate the glycol after the completion of the reaction depending on the use of the cyclic carbonate.

since the generated glycol has small difference in the boiling point from the cyclic carbonate, and they form an azeotropic mixture, separation by distillation is typically difficult. In order to increase the purity of the cyclic carbonate, rectification using a rectification column having many stages, and removal of a glycol by using means other than distillation such as crystallization and adsorption have been performed (Patent Literatures 6 and 7). However, as the stages of the purification step increases, more days for the steps are required, and the yield of the obtained cyclic carbonate is also decreased. Since the reaction heat of the reaction between the epoxide and carbon dioxide is high, circulation of a reaction liquid is generally performed (Patent Literature 2). However, if a reaction liquid in which a glycol exists together is circulated, a problem occurs that the activity of the catalyst is decreased.

Since it is difficult to separate thus-generated glycol from the cyclic carbonate in a simple manner, water adsorbed by a heterogenous catalyst is removed in advance before a reaction by heating a catalyst in a gas flow of an inert gas such as nitrogen at a high temperature in advance, or the like.

However, in a case when a catalyst in which an organic compound is immobilized on a support or the like is used, the organic chain is thermally decomposed even by heating at about 200° C. (about 150° C. in some cases), and thus there is a problem that the catalyst activity is rather decreased by heating. Furthermore, at such a low temperature that the catalyst is not deteriorated, even if heating is performed, the water adsorbed by the catalyst is not sufficiently removed, and thus a large amount of glycol is generated at an earlier stage of the reaction.

An object of the present invention is to provide a method for continuously producing a cyclic carbonate, by which generation of a glycol in a reaction for synthesizing a cyclic carbonate is suppressed, and a cyclic carbonate having a high purity can be efficiently obtained even by simple purification.

Solution to Problem

The present inventors conducted intensive studies, and found that, in a method for continuously producing a cyclic carbonate by a fixed bed continuous flow process, by bringing a pre-treatment liquid containing a cyclic carbonate into contact with a catalyst before feeding a carbon dioxide and an epoxide to a fixed-bed tube reactor, and removing the generated glycol outside of the system in advance, the generation of the glycol in the subsequent continuous reaction is significantly suppressed, and a cyclic carbonate having a high purity can be efficiently obtained even by simple purification, and thus completed the present invention.

That is, the present invention provides a method for continuously producing a cyclic carbonate, the method including filling a catalyst in a fixed-bed tube reactor, and continuously feeding carbon dioxide and an epoxide to the fixed-bed tube reactor to thereby bring the carbon dioxide and the epoxide into contact with the catalyst, while continuously withdrawing the reaction liquid in the fixed-bed tube reactor, in which the method includes a pre-treatment step in which a pre-treatment liquid containing a cyclic carbonate is brought into contact with the catalyst before feeding the carbon dioxide and the epoxide to the fixed-bed tube reactor, and the generated glycol is removed out of the system.

Advantageous Effects of Invention

According to the production method of the present invention, the generation of a glycol in a reaction for the synthesis of a cyclic carbonate is suppressed, and thus a cyclic carbonate having a high purity can be efficiently obtained even by a simple purification.

DESCRIPTION OF EMBODIMENTS

[Pre-Treatment Step]

Figure 1:
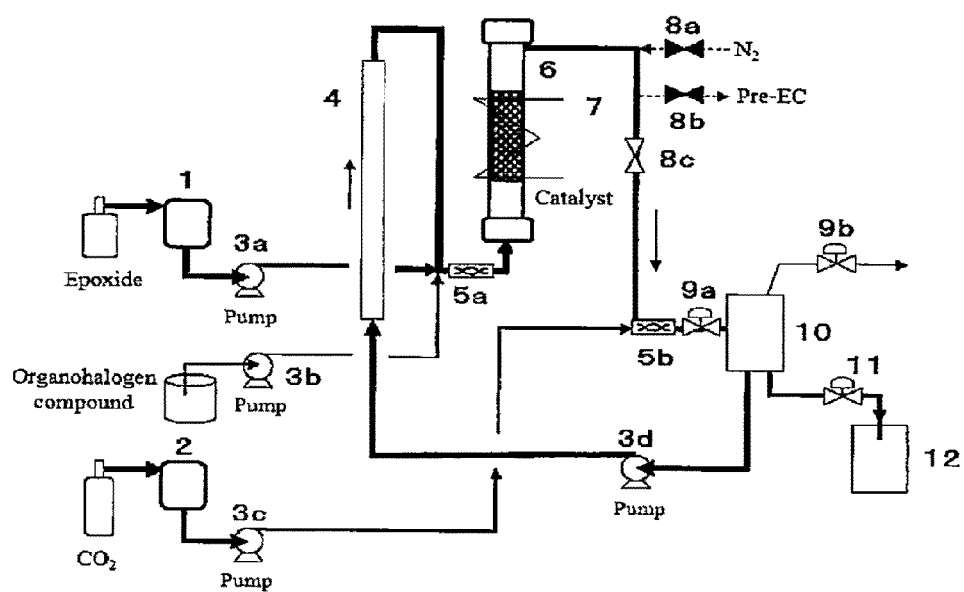
FIG. 1 is a schematic drawing showing an example of the continuous reaction apparatus used in the production method of the present invention.

The method for continuously producing a cyclic carbonate of the present invention is characterized by including a pre-treatment step in which a pre-treatment liquid containing a cyclic carbonate is brought into contact with the catalyst filled in a fixed-bed tube reactor before feeding the carbon dioxide and the epoxide to the fixed-bed tube reactor, and the generated glycol is removed out of the system. By bringing the pre-treatment liquid containing a cyclic carbonate into contact with the catalyst, the water adsorbed by the catalyst and the cyclic carbonate cause a reaction, and are converted to a glycol. Furthermore, by removing the generated glycol out of the system before feeding the raw materials, the incorporation of the glycol into the reaction system for the synthesis of the cyclic carbonate can be prevented. Furthermore, the liquid permeation of the pre-treatment liquid and the removal of the glycol may be performed continuously or intermittently, and it is preferable to perform continuously.

In addition, prior to the pre-treatment step, a reactor in which the catalyst is filled may be subjected to preliminary drying with vacuum exhausting and/or an inert gas. By such preliminary drying, the treatment time by the pre-treatment liquid can be shortened. It is preferable to perform the preliminary drying at a temperature close to the temperature when the pre-treatment liquid mentioned below is brought into contact with the above-mentioned catalyst. As the above-mentioned inert gas, helium, argon, nitrogen, carbon dioxide or the like can be used.

Furthermore, the temperature when the pre-treatment liquid is brought into contact with the above-mentioned catalyst is preferably in the range of from 20 to 140° C., more preferably from 50 to 130° C., and further more preferably from 80 to 120° C. By adjusting the temperature to be 20° C. or higher, the reaction between the cyclic carbonate and the water contained in the catalyst is promoted. Furthermore, according to the production method of the present invention, it is possible to sufficiently remove the water content in the catalyst by a glycol-generation reaction even when the temperature of the pre-treatment is a low temperature of 140° C. or lower, and the decomposition of the cyclic carbonate is rather suppressed by setting the temperature to 140° C. or lower, and the water in the catalyst can be removed more efficiently.

Furthermore, the contact time is generally from 1 to 40 hours From the viewpoint of sufficiently removing the water adsorbed by the catalyst, it is preferable to perform it until the total content of the glycol in the effluent from the reactor is 150 ppm or less, and more preferable to perform it until the total content becomes 100 ppm or less.

<Pre-Treatment Liquid>

The cyclic carbonate contained in the pre-treatment liquid is not especially limited. Examples include ethylene carbonate, propylene carbonate, butylene carbonate, isobutylene carbonate, trifluoromethylethylene carbonate, vinylethylene carbonate, cyclohexene carbonate, styrene carbonate, butadiene monocarbonate, butadiene dicarbonate, chloromethyl carbonate, pinene carbonate, tetracyanoethylene carbonate and the like, and these can be used alone or in combination of two or more kinds.

Among such cyclic carbonates, those represented by the following formula (1) are preferable. Furthermore, in view of the purity of the cyclic carbonate to be synthesized, it is preferable to use the same cyclic carbonate as those to be synthesized.

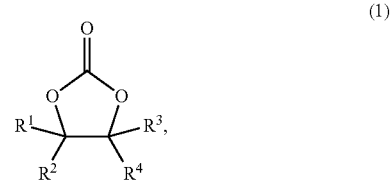

in the formula (1), $R^1$ and $R^2$ each independently represents a hydrogen atom, alkyl having carbon number of from 1 to 6, haloalkyl having carbon number of from 1 to 6, alkenyl having carbon number of from 2 to 6, haloalkenyl having carbon number of from 2 to 6, aryl having carbon number of from 6 to 12 or cyano, and $R^3$ and $R^4$ each independently represents a hydrogen atom, cyano or aryl having carbon number of from 6 to 12, provided that either $R^3$ or $R^4$ may form cycloalkyl together with either $R^1$ or $R^2$.

The carbon number of the alkyl and haloalkyl represented by the above-mentioned $R^1$ and $R^2$ are each preferably from 1 to 4. Examples of the alkyl include methyl, ethyl, propyl and butyl, preferably methyl and ethyl, and more preferably methyl.

The carbon number of the alkenyl and haloalkenyl represented by the above-mentioned $R^1$ and $R^2$ are each preferably from 2 to 4, and vinyl and the like are specifically exemplified.

Examples of the halogen atom in the haloalkyl and haloalkenyl include fluorine, chlorine, bromine, iodine and the like.

As the aryl represented by the above-mentioned $R^1$, $R^2$, and $R^4$, phenyl is preferable.

Among $R^3$ and $R^2$ as mentioned above, hydrogen, alkyl having a carbon number of from 1 to 6, and haloalkyl having a carbon number of from 1 to 6 are preferable.

Furthermore, hydrogen is preferable as $R^3$ and $R^4$.

As the above-mentioned cyclic carbonate, a commercially available cyclic carbonate can be purchased and used, and the cost can be decreased by using the reaction liquid before the renewal of the catalyst obtained in the synthesis of the cyclic carbonate, the circulation liquid, or liquids obtained by purifying these, or the like.

<Catalyst>

The catalyst used in the production method of the present invention is not specifically limited as long as it has an activity on the synthesis of the cyclic carbonate from the epoxide and carbon dioxide and can be filled in a fixed-bed tube reactor, and a solid catalyst in which an organic compound (preferably an ionic organic compound) is immobilized on a support is preferable in view of the reaction efficiency. In the case when the above-mentioned solid catalyst is used as the catalyst, and the temperature of the above-mentioned pre-treatment is 140° C. or lower, the decrease of the catalyst activity by the thermal decomposition of the organic chain can be suppressed, and thus the reaction efficiency is dramatically improved.

Examples of the above-mentioned ionic organic compound include quaternary organic onium salts selected from quaternary organic ammonium salts each having a halide anion as a counterion and quaternary organic phosphonium salts each having a halide anion as a counterion, and these can be used alone or in combination of two or more kinds. Examples of the halogen in the above-mentioned halide anion include fluorine, chlorine, bromine and iodine. Furthermore, examples of the organic groups that are bound to the nitrogen atom or phosphorus atom in the above-mentioned quaternary organic onium salt include groups that induce $R^5$ mentioned below, $R^6$ to $R^8$.

Among the above-mentioned quaternary organic onium salts, tetraalkylammonium salts such as tetraalkylammonium chlorides and tetraalkylammonium bromides; and tetraalkylphosphonium salts such as tetraalkylphosphonium chlorides and tetraalkylphosphonium bromides are preferable, and tetraalkylphosphonium salts are more preferable.

Examples of the above-mentioned support include inorganic oxide supports and organic polymer supports. The shape thereof is preferably a particulate form, and a porous form is preferable.

As the above-mentioned inorganic oxide support, those containing oxides of silicon, aluminum, titanium, magnesium, zirconium, boron, calcium, zinc, barium, iron and the like are preferable, and one kind or two or more kinds of such oxides may be contained. Examples of such oxides include $SiO_2$, $Al_2O_3$, $TiO_2$, $MgO$, $ZrO_2$, $B_2O_3$, $CaO$, $ZnO$, $BaO$, and $Fe_2O_3$.

Preferable specific examples of the inorganic oxide support include a silica gel (gelled silica), mesoporous silica, ceramics, zeolite and porous glass, and a silica gel and mesoporous silica are preferable.

Furthermore, examples of the above-mentioned organic polymer support include polystyrenes, polystyrene copolymers, poly(meth)acrylate, poly(meth)acrylamide, polyimides, polybenzimidazole, polybenzoxazole, polybenzothiazole, polyethylene glycol and polypropylene glycol, or copolymers and polymer blends containing these polymers as major components, and the like.

As a preferable specific example of the catalyst used in the production method of the present invention, a catalyst in which the group of the following formula (2) is bound to the above-mentioned support is exemplified.

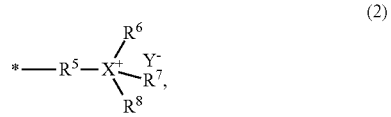

(2)

in the formula (2), represents alkylene, arylene, alkarylene, arylenealkylene or alkylenearylene, $R^6$ to $R^8$ each independently represents alkyl, aryl, aralkyl, alkoxyalkyl, aryl having alkoxy as substituent, or a group in which one or more of the hydrogen atom contained in any of these groups has/have been substituted with group(s) containing hetero atom(s), X represents a phosphorus atom or a nitrogen atom, Y represents a halogen atom, and * represents a bond.

In the above-mentioned formula (2), the alkylene represented by $R^5$ may have either a linear form or a branched chain form, and the carbon number thereof is preferably from 1 to 8, more preferably from 1 to 6, and further more preferably from 2 to 4.

Examples of the above-mentioned alkylene include methylene, ethylene, trimethylene, propylene, tetramethylene, pentamethylene, hexamethylene, heptamethylene, octamethylene and the like.

Furthermore, the carbon number of the arylene of $R^5$ is preferably from 6 to 14, more preferably from 6 to 12, and further more preferably from 6 to 10. Examples include bivalent groups derived from benzene, naphthalene, anthracene, phenanthrene, biphenyl and the like.

Furthermore, the alkarylene represented by $R^5$ is preferably alkarylene having a carbon number of from 8 to 10, and examples include xylylene and the like.

Furthermore, the carbon numbers of the arylenealkylene and alkylenearylene represented by $R^5$ are each preferably from 7 to 12, and more preferably from 7 to 10.

Examples of the above-mentioned arylenealkylene include phenylenemethylene, phenyleneethylene, phenylenetrimethylene, naphthylenemethylene, naphthyleneethylene and the like.

Furthermore, examples of the above-mentioned alkylenearylene include methylenephenylene, ethylenephenylene, trimethylenephenylene, methylenenaphthylene, ethylenenaphthylene and the like.

Among $R^5$ mentioned above, alkylene, arylene and arylenealkylene are preferable, and alkylene is more preferable.

The alkyl represented by $R^6$ to $R^8$ in the formula (2) may have either a linear form, a branched chain form or a cyclic form, and the carbon number thereof are each preferably from 1 to 8, more preferably from 1 to 6, and furthermore preferably from 2 to 4.

Examples of the above-mentioned alkyl include methyl, ethyl, propyl, isopropyl, butyl, isobutyl, pentyl, hexyl, heptyl, octyl, cyclohexyl and the like.

The carbon numbers of the aryl represented by $R^6$ to $R^8$ are each preferably from 6 to 14, more preferably from 6 to 12, and further more preferably from 6 to 10. Examples include phenyl, naphthyl, anthryl, biphenyl, phenanthryl and the like.

The carbon number of aralkyl represented by $R^6$ to $R^8$ are each preferably from 7 to 12, and more preferably from 7 to 10. Examples include benzyl, phenethyl, phenylpropyl, naphthylmethyl, naphthylethyl and the like.

The alkoxyalkyl represented by $R^6$ to $R^8$ are each preferably alkoxyalkyl having a carbon number of from 2 to 8, and examples include methoxyethyl and the like. The aryl having alkoxy(s) as substituent(s) of $R^6$ to $R^8$ are each preferably alkoxyaryl having carbon number of from 7 to 14, and examples include methoxyphenyl, dimethoxyphenyl and the like. Furthermore, the number and posit n(s) of the alkoxy possessed by the aryl are optional, and the number of the alkoxy is a preferably from 1 to 4, and more preferably from 1 or 2.

In addition, in the above-mentioned alkyl, aryl, aralkyl, alkoxyalkyl and aryl having alkoxy as substituent, one or more of hydrogen atom(s) included in any of these groups may be substituted with group(s) containing hetero atom(s). Examples of the hetero atoms include nitrogen, oxygen, phosphorus, sulfur, halogen atoms (a fluorine atom and the like) and the like.

Examples of the above-mentioned groups containing hetero atom(s) include nitrogen-containing groups such as amino, hydrazino, nitro, cyano, isocyano and amidino; oxygen-containing groups such as alkanoyl, carboxy, alkoxycarbonyl and hydroxy; phosphorus-containing groups such as phosphanyl, phosphono and phosphinyl; sulfur-containing groups such as sulfa, sulfanyl, alkylsulfanyl, alkylsulfonyl, alkylsulfonylamino, alkylaminosulfonyl, alkylsulfinyl, alkylaminosulfinyl, alkylsulfinylamino and thiocarboxy, and the like.

Among $R^6$ to $R^8$ as mentioned above, alkyl, aryl and aralkyl are preferable.

In the formula (2), a phosphorus atom is preferable as X. Furthermore, examples of the halogen atom of Y include a fluorine atom, a chlorine atom, a bromine atom and an iodine atom, and a chlorine atom and a bromine atom are preferable.

In addition, the group represented by the above-mentioned formula (2) may be directly bound to the support by a covalent bond or the like, or may be bound through a linker as in the following formula (3).

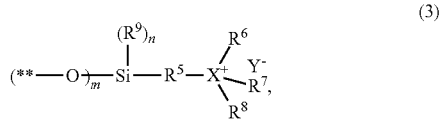

(3)

in the formula (3), represents methyl or ethyl, n represents an integer of 0 to 2, and m represents an integer of 1 to 3, and when n+m=3 is satisfied and n is 2, the two $R^9$s may be the same or different. ** represents a part that is linked to the support, and the other symbols are as defined above.

Among these, those having structures in which n=0 and are preferable.

Furthermore, as the above-mentioned catalyst, a catalyst having a halogen modification amount of from 0.25 to 0.8 mmol/g and a phosphorus or nitrogen modification amount of from 0.25 to 0.6 mmol/g is preferable.

Furthermore, the amount of the catalyst to be filled in the reactor is generally from 0.01 to 10 parts by mass, preferably from 0.03 to 10 parts by mass with respect to 100 parts by mass of the whole amount of the epoxide to be fed.

As the catalyst used in the product ion method of the present invention, a commercially available catalyst may be used, or the catalyst may be prepared by, for example, reacting a silane compound containing a halogen with a silica gel, and reacting this with an organic phosphine such as a trialkylphosphine to form a phosphonium salt, according to the methods described in WO 2005/084801 A and JP 2008-296066 A.

[Continuous Reaction Step]

The method for continuously producing a cyclic carbonate of the present invention employs carbon dioxide and an epoxide as raw materials, and it is preferable to feed these to a fixed-bed tube reactor so that these are mixed.

Furthermore, it is preferable that a liquid of a cyclic carbonate is continuously fed to the reactor, prior to a continuous reaction, after the above-mentioned pre-treatment step, and this liquid of the cyclic carbonate is continuously withdrawn from the reactor and circulated in advance, and the carbon dioxide and the epoxide are fed to the reactor under the condition. By this way, the above-mentioned raw material and the agent for suppressing catalyst deterioration mentioned below are put into a state that they are dissolved in the cyclic carbonate (the cyclic carbonate acts as a solvent), and the reaction state can be deemed as a pseudo liquid-solid reaction with the catalyst. Therefore, the temperature rising due to the reaction heat is mitigated, the wettability of the catalyst is improved, and the drifting of the carbon dioxide gas is suppressed. As the cyclic carbonate, the cyclic carbonate contained in the above-mentioned pre-treatment liquid may be used.

The above-mentioned epoxide is not especially limited as long as it contains at least one epoxy ring (a three-membered ring formed of two carbon atoms and one oxygen atom) in the structural formula. Examples include ethylene oxide, propylene oxide, butylene oxide, isobutylene oxide, vinylethylene oxide, trifluoromethylethylene oxide, cyclohexene oxide, styrene oxide, butadiene monoxide, butadiene dioxide, 2-methyl-3-phenylbutene oxide, pinene oxide, tetracyanoethylene oxide and the like.

Among such epoxides, those represented by the following formula (4) are preferable, and ethylene oxide and propylene oxide are more preferable.

(4)

in the formula (4), to $R^4$ are as defined above.

The total feed amount of the carbon dioxide is generally from 1.0 to 10 mol equivalent amount, preferably from 1.1 to 2.0 mol equivalent amount with respect to the whole amount of the epoxide to be fed.

Furthermore, a solvent may be used in the continuous reaction step. As such a solvent, besides the above-mentioned cyclic carbonates, aliphatic hydrocarbons such as pentane, hexane and heptane; aromatic hydrocarbons such as benzene and toluene; alcohols such as methanol and ethanol; ketones such as acetone and methyl ethyl ketone; ethers such as diethyl ether, methyl-tert-butyl ether, tetrahydrofuran and dioxane; amides such as dimethylformamide and dimethylacetamide; esters such as ethyl acetate; tertiary amines such as triethylamine, pyridine, methylpyridazine and N,N'-dimethylpyridazinone; sulfides such as dibutylsulfide; phosphines such as tributylphosphine, and the like can be used. These solvents may be used by one kind alone or in combination of two or more kinds.

Furthermore, the use amount of the above-mentioned solvent is an amount that the concentration of the epoxide in the reactor is generally 1.0 to 20% by mass.

Furthermore, in the production method of the present invention, an agent for suppressing catalyst deterioration may be fed to the reactor together with the above-mentioned raw materials. In the case when the above-mentioned solid catalyst in which a quarternary organic onium salt is immobilized on a support is used, an organic halide is preferable as the agent for suppressing catalyst deterioration. Examples of the organic halide include alcohol halides such as bromoethanol and chloroethanol; alkyl halides; ether halides; carbonyl halide compounds, and the like, and one kind may be used alone, or two or more kinds may be used in combination.

Furthermore, the above-mentioned agent for suppressing catalyst deterioration is generally added so that the concentration of the agent for suppressing catalyst deterioration in the reactor is 0.01 to 0.2% by mass.

The reaction temperature in the continuous reaction step is preferably in the range of from 20 to 160° C., and more preferably from 50 to 150° C. in view of reaction efficiency.

In the case when a solid catalyst in which an organic compound is immobilized on a support is used, the reaction temperature is further preferably in the range of from 80 to 140° C., more preferably from 80 to 130° C., and especially preferably from 80 to 120° C.

Furthermore, the reaction pressure is not especially limited, and is preferably in the range of from 0.1 to 100 MPa, more preferably from 0.5 to 50 MPa, and further more preferably from 1 to 25 MPa.

In the production method of the present invention, it is preferable to feed a part of the reaction liquid that has been continuously withdrawn from the fixed-bed tube reactor to the fixed-bed tube reactor, and circulate the reaction liquid. In the present invention, due to low amount of glycol in the obtained reaction liquid, the activity of the catalyst is hardly reduced even with the circulation as mentioned above, and the inside of the reactor is diluted with cyclic carbonate by conducting the circulation, and thus the temperature in the reactor is easily controlled.

The production method of the present invention can be performed by using a continuous production apparatus having a fixed-bed tube reactor, and the continuous production apparatus shown in FIG. 1 is exemplified as an example of such continuous production apparatus. This apparatus includes pumps (3a) and (3c) that respectively send an epoxide and carbon dioxide to a reactor (6), and a circulation pump (3d). The reaction liquid that has flown out of the reactor (6) is once stored in a gas-liquid separation bath (10), and a predetermined amount is fed therefrom to the reactor (6) by the pump (3d), whereby the reaction liquid is circulated. The residual reaction liquid is sent to a receiving tank (12).

Then, a cyclic carbonate having a high purity can be obtained by collecting the reaction liquid of the above-mentioned continuous reaction. Such a reaction liquid may be separated and purified as necessary by suitably combining conventional means such as general methods such as distillation, adsorption and crystallization, and these methods may be either of a batch system or a continuous system. Since the reaction liquid contains the cyclic carbonate at a high purity and contains the glycol at a low amount, in the case when separation and purification are performed, a cyclic carbonate having a high purity can be obtained even by a simple means. In addition, the glycol concentration in the collected reaction liquid is generally 100 ppm or less, preferably 50 ppm or less, more preferably 20 ppm or less, and especially preferably 10 ppm or less.

The obtained cyclic carbonate has a structure in which the epoxy ring of the epoxide has been converted to a carbonate ring (a 5-membered ring having an O—CO—O bond), and specific examples include those cyclic carbonate contained in the pre-treatment liquid, as described above.

EXAMPLES

The present invention will be explained below in detail with exemplifying Examples. However, the present invention is not limited to these Examples.

The analysis methods used in the respective Examples and Comparative Examples are as follows.

(1) Fluorescence X-Ray Analysis

For the measurement of the bromine, chlorine and phosphorus modification amounts of the catalyst, a fluorescence X-ray analysis was used (apparatus: product name "System 3270" (manufactured by Rigaku Corporation), measurement conditions: Rh bulb tube, tube voltage 50 kV, tube current 50 mV, vacuum atmosphere, detector: SC, F-PC).

(2) Gas Chromatography

Gas chromatography was used for the analysis of the compositions of the reaction liquid and the like. The conditions for the analysis are as follows.

Apparatus: product name "GC-2010 Plus" (manufactured by Shimadzu Corporation)
Detector: FID
INJ temperature: 150° C.
DET temperature: 260° C.
Sample amount: 0.3 µL
Split ratio: 5
Column: DB-624 (60 m, 0.32 mmID, 1.8 µm, manufactured by Agilent Technologies)
Column temperature: 70° C., 3 minutes–5° C./min–120° C.–10° C./min–250° C., 5 minutes (31 minutes in total)

Catalyst Synthesis Example 1

Synthesis of Tributylphosphonium Bromide Surface-Modified Silica Gel Catalyst 2,000 g of a bead-like silica gel (CARiACT Q-10 manufactured by Fuji Silycia Chemical, Ltd. (average fine pore diameter 10 nm, particle diameter 1.2 to 2.4 mm, specific surface area 300 m$^2$/g)) and 5,000 mL of xylene were charged into a 10 L three-necked flask with agitator blades equipped with a Dean-Stark trap, and azeotropic dehydration of xylene-water was performed under reflux at 140° C. for 2 hours to thereby remove the water in the silica gel. The Dean-Stark trap was then removed, the inside of the flask was purged with nitrogen, and 219 g (0.846 mol) of 3-bromopropyltrimethoxysilane was added dropwise thereto. This was directly refluxed under heating at 135° C. for 7 hours to perform a silanation reaction. The obtained reaction product was then separated by filtration, and washed twice with xylene to give 3,810 g of a catalyst precursor containing xylene (a bromopropylated silica gel). The obtained catalyst precursor and 5,000 mL of xylene were then charged into a 10 L three-necked flask with agitator blades, the inside of the flask was purged with nitrogen, and 453 g of tri-n-butylphosphine was added dropwise thereto. This was directly heated at 120° C. for 25 hours to perform a quaternary phosphoniumization reaction. After the reaction, the reaction product was separated by filtration, and washed with acetone six times. The obtained reaction product was dried under a nitrogen airflow at 120° C. for 5 hours under a reduced pressure to give 2,328 g of the intended tributylphosphonium bromide surface-modified silica gel. The bromine modification amount in the catalyst was 0.35 mmol/g, and the phosphorus modification amount was 0.32 mmol/g.

Example 1

Ethylene Carbonate Production Example (1)

An ethylene carbonate was produced by using the continuous circulation-type reaction apparatus shown in FIG. 1.
<Pre-Treatment Step>

(1-1) A reactor 6 having an inner diameter of 50 mm, a length of 100 cm and a volume of 2,000 mL was filled with 530 g (an amount that fills up to the scale of 1,000 mL of the reactor 6) of the catalyst obtained in Catalyst Synthesis Example 1, and the front and back of the catalyst were each filled with glass beads having a particle diameter of 4 mm.

(1-2) A valve 8a was then opened, nitrogen was fed to the reactor 6 at 1 L/min, and boiled water was further flowed into a reactor jacket 7 to thereby raise the temperature of the reactor 6 to 100° C. The catalyst was subjected to preliminary drying while the nitrogen was continuously flowed for 8 hours, and the catalyst drying by the nitrogen circulation was stopped by closing the valve 8a.

(1-3) Subsequently, 10 kg of an ethylene carbonate that had been dissolved by heating at 70° C. in advance as a pre-treatment liquid was put into a gas-liquid separation bath 10, and this liquid was transferred to the preheater 4 and reactor 6 by the pump 3d at 1,250 g/h for 8 hours. At that time, the pre-treatment liquid that was fed to the reactor 6 was heated in the preheater 4 at a temperature at which the temperature of the reactor inlet was 100° C., and the pre-treatment liquid that has been ejected from the reactor 6 was continuously withdrawn out of the system from the bubble 8b by closing the valve 8c.

The concentration of the monoethylene glycol (hereinafter MEG) in the pre-treatment liquid that had been ejected from the reactor 6 after 8 hours had passed from the initiation of the liquid sending of the pre-treatment liquid was 43 ppm, and the concentration of the diethylene glycol (hereinafter DEG) was 29 ppm. After the glycol concentration had been confirmed, the pre-treatment was completed by closing the valve 8b by opening the valve 8c.

<Continuous Reaction>

(2-1) 7 kg of an ethylene carbonate that had been dissolved by heating at 70° C. in advance was put into the gas-liquid separation bath 10, and this was transferred to the preheater 4 and reactor 6 at 1,200 g/h by the pump 3d. At that time, the ethylene carbonate that was fed to the reactor 6 was heated in the preheater 4 at a temperature at which the temperature of the reactor inlet was 100° C. The effluent from the reactor 6 was circulated in the system through the valve 8c.

(2-2) Next, carbon dioxide was fed to the reactor 6 by the pump 3c at 300 g/h, and the pressures of the gas-liquid separation bath 10, preheater 4 and reactor 6 were adjusted so as to be 7 MPa by a back pressure valve 9b. At that time, the carbon dioxide was stirred by a static mixer 5b, and fed to the preheater 4 and reactor 6 in the state that the carbon dioxide was dissolved in the ethylene carbonate.

Subsequently, the flow amount of the carbon dioxide was adjusted to 45 g/h and the flow amount of the ethylene carbonate in which the carbon dioxide was dissolved was adjusted to 1,400 g/h, respectively, by the pumps 3c and 3d, and the pressures of the preheater 4 and reactor 6 were adjusted to 7.5 mPa by the back pressure valve 9a.

(2-3) About 20 hours after the initiation of the circulation of the ethylene carbonate in the above-mentioned step (2-1), 2-bromoethanol was fed to the reactor 6 at 0.43 g/h by the pump 3b, and the ethylene oxide was fed to the reactor 6 at 30 g/h by the pump 3a, whereby a continuous circulation-type reaction was initiated.

In addition, in the feeding of the 2-bromoethanol and ethylene oxide, the 2-bromoethanol and ethylene oxide were mixed with the ethylene carbonate by a static mixer 5a, and fed to the reactor 6. That is, all of the ethylene oxide, carbon dioxide and 2-bromoethanol are fed to the reactor 6 in the state that they are dissolved in the ethylene carbonate. By circulating the ethylene carbonate in this way, the reaction state can be deemed as a pseudo liquid-solid reaction with the catalyst.

(2-4) 6 after the initiation of the reaction, the flow amount of the 2-bromoethanol was adjusted to 0.024 g/h by the pump 3b so that the feed amount of the 2-bromoethanol to the reactor 6 became constant at 2-bromoethanol/ethylene oxide=5 mmol/mol, and the reaction was continued. The ethylene carbonate generated by the reaction was withdrawn to a receiving tank 12 by a liquid level-adjusting valve 11.

Figure 2:
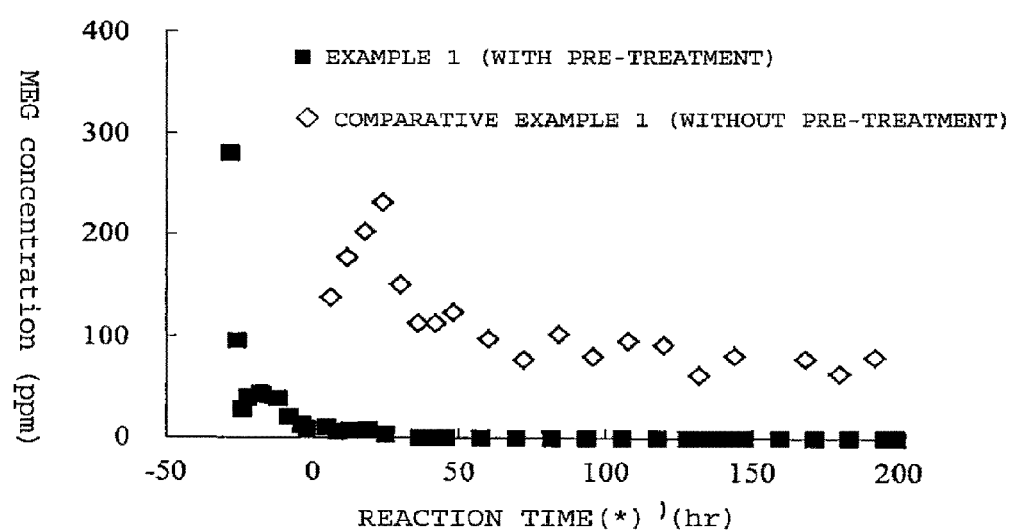
FIG. 2 is a drawing showing the change over time of the concentration of the monoethylene glycol in the effluent in Example.
Figure 3:
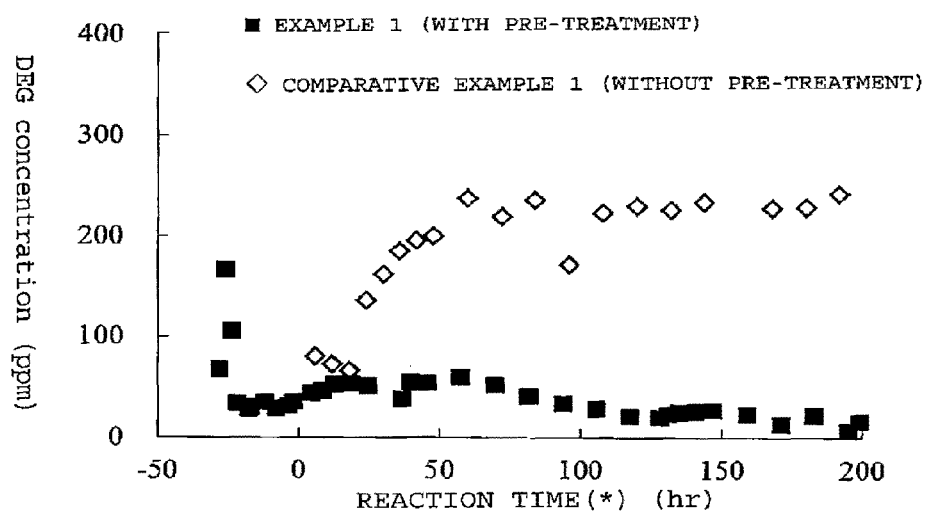
FIG. 3 is a drawing showing the change over time of the concentration of the diethylene glycol in the effluent in Example.

The transitions of the concentrations of MEG and DEG in the effluent from the reactor 6 from the initiation of the above-mentioned step (1-3) to the completion of the reaction were plotted. The results are shown in FIGS. 2 and 3, respectively. Furthermore, the concentration of the ethylene carbonate in the reaction liquid at 195 hours after the initiation of the reaction was 99.6%, MEG was not detected (detection lower limit: 4 ppm), and the concentration of DEG was 7 ppm.

The reaction liquid at 195 hours' time after the initiation of the above-mentioned reaction was subjected to distillation purification by using a batch type Older shaw rectification column with ten actual stages under conditions of a column top pressure of 10 torr, a column bottom temperature of 120 to 122° C. and a reflux rate of 60 (up to a distillation rate of 5% by mass with respect to the charged liquid amount), and distillation purification was further performed by changing the reflux rate to 4. The obtained purified ethylene carbonate had a purity of 99.99%, and neither MEG nor DEG was detected (both were at a detection lower limit of 4 ppm).

Comparative Example 1

Ethylene Carbonate Preparation Example (2)

A continuous reaction was performed by similar operations to those in Example 1, except that the above-mentioned step (1-3) was not conducted. The transitions of the concentrations of MEG and DEG in the effluent from the reactor 6 from the initiation to the completion of the reaction were plotted. The results are shown in FIGS. 2 and 3, respectively. Furthermore, the concentration of the ethylene carbonate in the reaction liquid at 192 hours after the initiation of the reaction was 99.0%, the concentration of MEG was 80 ppm, and the concentration of DEG was 241 ppm.

The reaction liquid at 192 hours' time after the initiation of the above-mentioned reaction was subjected to distillation purification by using a batch type Older shaw rectification column with ten actual stages in a similar manner to that in Example 1. The obtained purified ethylene carbonate had a purity of 99.95%, the concentration of MEG was 32 ppm, and the concentration of DEG was 256 ppm.

Reference Example

Evaluation of Effect on Catalyst Deterioration by Addition of Glycols

The following batch-type ethylene carbonate synthesis reaction shows that glycols cause decrease in the activity of a catalyst.

200 mg of a tributylphosphonium bromide surface-modified silica gel catalyst (average fine pore diameter: 10 nm, particle diameter: 1.2 to 2.4 mm, bromine modification amount 0.28 mmol/g, phosphorus modification amount: 0.30 mmol/g), which was synthesized in a similar manner to that in the above-mentioned Synthesis Example, was charged in a 50 mL autoclave containing a stirrer, and dried at 120° C. for 1 hour under a reduced pressure. The inside of the autoclave was returned to atmospheric pressure and room temperature with nitrogen, and 3 g of ethylene oxide (about 68 mmol) and the glycol shown in Table 1 were charged.

Carbon dioxide was then temporarily filled up to 1.5 MPa, and the inside of the autoclave was then heated to 120° C. while stirring was conducted by a rotor at 800 rpm, the inner pressure was adjusted to 4.5 MPa by further filling carbon dioxide, and a reaction was conducted for 1 hours. After the cooling, the residual carbon dioxide was released, and the inside of the autoclave was depressurized. The obtained reaction liquid was analyzed by gas chromatography, and the conversion rate of the ethylene oxide and the yield of the ethylene carbonate were obtained. The result is shown in Table 1.

TABLE 1

| Glycol | Addition amount of glycol (mmol) | Conversion rate of ethylene oxide (%) | Yield of ethylene carbonate (%) | Detection amount of 2-bromoethanol (mmol) |
|---|---|---|---|---|
| None | 0 | 27 | 27 | 3 |
| MEG | 1.5 | 23 | 23 | 9 |
| MEG | 7 | 18 | 18 | 20 |
| MEG | 14 | 14 | 14 | 34 |
| DEG | 1 | 24 | 24 | 6 |
| DEG | 4 | 20 | 20 | 9 |
| DEG | 8 | 19 | 19 | 11 |

REFERENCE SIGNS LIST

1: ethylene oxide storage tank
2: carbon dioxide storage tank
3a to 3d: pump
4: preheater
5a to 5b: static mixer
6: reactor
7: reactor jacket
8a to 8c; valve
9a to 9b: back pressure valve
10: gas-liquid separation bath
11: liquid level-adjusting valve
12: receiving tank

The invention claimed is:

1. A method for continuously producing a cyclic carbonate, the method comprising:
    filling a tributylphosphonium bromide surface-modified silica gel catalyst in a fixed bed tube reactor,
    contacting a pre-treatment liquid comprising a sacrificial cyclic carbonate with the catalyst to form a glycol,
    removing the glycol from the fixed-bed tube reactor, and
    continuously feeding carbon dioxide, 2-bromoethanol and ethylene oxide to the fixed-bed tube reactor to thereby bring the carbon dioxide and the ethylene oxide into contact with the tributylphosphonium bromide surface-modified silica gel catalyst to form a reaction liquid comprising the cyclic carbonate, while continuously withdrawing the reaction liquid from the fixed-bed tube reactor,
    wherein the sacrificial cyclic carbonate and the cyclic carbonate in the reaction liquid are identical.

2. The method according to claim 1, wherein the pre-treatment liquid and the catalyst are brought into contact until a total amount of the glycol in an effluent from the fixed-bed tube reactor is 100 ppm or lower.

3. The method according to claim 1, wherein the pre-treatment liquid and the catalyst are brought into contact at a temperature in a range of 20° C. to 140° C.

4. The method according to claim 1, further comprising feeding a part of the reaction liquid that has been withdrawn to the fixed-bed tube reactor.

5. The method according to claim 1, further comprising drying said tributylphosphonium bromide surface-modified silica gel catalyst in said fixed-bed tube reactor by vacuum exhausting and/or by contact with an inert gas prior to said contacting said pre-treatment liquid with the catalyst.

* * * * *